United States Patent [19]

Haga et al.

[11] Patent Number: 4,677,111
[45] Date of Patent: Jun. 30, 1987

[54] N-BENZOYL-N'-(3-NITROPHENYL) UREA COMPOUNDS, AND ANTITUMOROUS COMPOSITIONS CONTAINING THEM

[75] Inventors: Takahiro Haga, Kusatsu; Nobutoshi Yamada; Hideo Sugi, both of Moriyama; Toru Koyanagi, Kyoto; Hiroshi Okada, Kusatsu, all of Japan

[73] Assignee: Ishihara Sangyo Kaisha Ltd., Osaka, Japan

[21] Appl. No.: 782,570

[22] Filed: Oct. 1, 1985

[30] Foreign Application Priority Data

Oct. 12, 1984 [JP] Japan ................................ 59-213718

[51] Int. Cl.$^4$ ................... A61K 31/505; A61K 31/50; C07D 239/30; C07D 237/12
[52] U.S. Cl. ..................................... 514/274; 546/221; 514/247; 544/316; 544/239; 544/241
[58] Field of Search ..................... 544/316, 239, 241; 546/221; 514/247, 274

[56] References Cited

U.S. PATENT DOCUMENTS

B 435,617  3/1976  Johnston ........................ 260/256.4
4,310,530  1/1982  Nishiyama et al. ............. 546/291

FOREIGN PATENT DOCUMENTS 25363    3/1981  European Pat. Off.
15272    2/1981  Japan.
99569    6/1982  Japan.
109721   7/1982  Japan.
2058072  8/1981  United Kingdom.

OTHER PUBLICATIONS

*Patents Abstracts of Japan*, vol. 6, No. 202 (C–129), [1980], Oct. 13, 1982, Abstracts of JP-57-109721.
*Patents Abstracts of Japan*, vol. 5, No. 62, (C–52), [734], Apr. 25, 1981, Abstract of JP-56-15272.

*Primary Examiner*—John M. Ford
*Attorney, Agent, or Firm*—Oblon, Fisher, Spivak, McClelland & Maier

[57] ABSTRACT

An N-benzoyl-N'-(3-nitrophenyl) urea compound having the formula

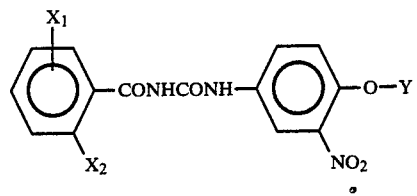

wherein each of $X_1$ and $X_2$ is a hydrogen atom, a halogen atom, a trifluoromethyl group or a nitro group, and Y is

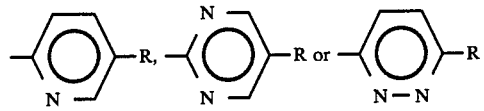

(wherein R is a hydrogen atom, a halogen atom or a tirfluoromethyl group), provided that when Y is

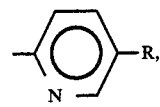

$X_1$ and/or $X_2$ is a nitro group. The compound is useful as an active ingredient of an antitumorous composition.

13 Claims, No Drawings

N-BENZOYL-N'-(3-NITROPHENYL) UREA COMPOUNDS, AND ANTITUMOROUS COMPOSITIONS CONTAINING THEM

BACKGROUND OF THE INVENTION

1. Field of the Invention

The present invention relates to novel N-benzoyl-N'-(3-nitrophenyl) urea compounds, antitumorous compositions containing them as active ingredients, a method for therapy of cancer by using these compounds, and a process for producing these compounds. More particularly, the present invention relates to the novel compounds including N-benzoyl-N'-(4-pyridyloxy-3-nitrophenyl) urea compounds, N-benzoyl-N'-(4-pyrimidinyloxy-3-nitrophenyl) urea compounds and N-benzoyl-N'-(4-pyridazinyloxy-3-nitrophenyl) urea compounds.

2. Discussion of the Background

Compounds similar to the compounds of the present invention are disclosed in the following publications. Namely, N-benzoyl-N'-pyridyloxyphenyl urea compounds are disclosed in (1) U.S. Pat. No. 4,310,530, (2) Japanese Unexamined Patent Publication No. 99569/1982, and (3) Japanese Unexamined Patent Publication No. 109721/1982, and N-benzoyl-N'-pyrimidinyloxyphenyl urea compounds are disclosed in (3) Japanese Unexamined Patent Publication No. 109721/1982. Further, N-benzoyl-N'-pyridazinyloxyphenyl urea compounds are disclosed in (4) Japanese Unexamined Patent Publication No. 15272/1981.

In the above publications (1), (2) and (4), it is disclosed that these compounds are useful as pesticides, particularly as insecticides. However, the above publications contain no indication that the compounds of the present invention have high antitumour activities. In the publication (3), it is disclosed that these compounds are useful as antitumour drugs. However, there is no description that the compounds of the present invention have much higher antitumour activities.

SUMMARY OF THE INVENTION

The present inventors have conducted extensive studies on the changes of the substituents for N-benzoyl-N'-substituted phenyl urea compounds, and have finally found that novel N-benzoyl-N'-(3-nitrophenyl) urea compounds having a certain specific substituent i.e. a nitro group at the 3-position of the phenyl group which is directly bonded to the urea group, have high antitumour activities. The compounds of this type are generally hardly soluble in both water and organic solvents, and accordingly poorly absorbable by the gut. Therefore, depending upon the manner of administration, they sometimes hardly exhibit antitumour activities, and there is a limitation for the intraperitoneal administration of such drugs for curing purposes. Whereas, it has been found that the compounds of the present invention are practically useful for the treatment of tumour or cancer and exhibit excellent antitumour activities by a simple manner of administration and in a simple formulation for the administration without bringing about side effects. The present invention is based on these discoveries.

DETAILED DESCRIPTION OF THE PREFERRED EMBODIMENTS

Namely, the present invention provides an N-benzoyl-N'-(3-nitrophenyl) urea compound having the formula:

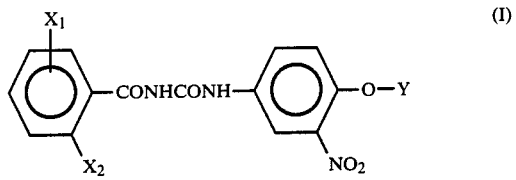

wherein each of $X_1$ and $X_2$ is a hydrogen atom, a halogen atom, a trifluoromethyl group or a nitro group, and Y is

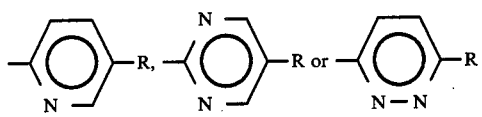

(wherein R is a hydrogen atom, a halogen atom or a trifluoromethyl group), provided that when Y is

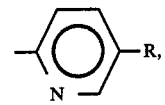

$X_2$ is a nitro group. The present invention also provides an antitumorous composition containing such a compound as the active ingredient, a method for therapy of cancer by using such a compound, and a process for producing such a compound. Now, the present invention will be described in detail with reference to the preferred embodiments. In the above-mentioned formula I, $X_1$ is preferably a hydrogen atom, $X_2$ is preferably a halogen atom or a nitro group, Y is preferably

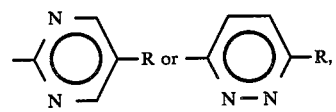

and R is preferably a halogen atom or a trifluoromethyl group. Particularly preferred is a case where $X_2$ is a nitro group, Y is

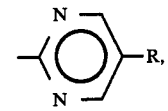

and R is a halogen atom.

As the halogen atom for $X_1$ $X_2$ and R in the formula I, there may be mentioned a fluorine atom, a chlorine atom, a bromine atom or an iodine atom.

The N-benzoyl-N'-(3-nitrophenyl) urea compound of the above-mentioned formula I, may be prepared, for instance, as follows:

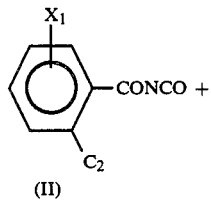
(II)

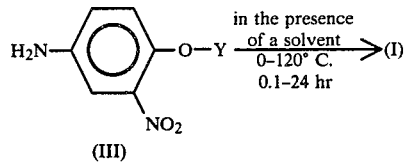
(III)

In the above formula, $X_1$, $X_2$ and Y are as defined above. As the solvent to be used in the above reaction, there may be mentioned benzene, toluene, xylene, monochlorobenzene, pyridine, dioxane, tetrahydrofuran, dimethyl sulfoxide, dimethylacetamide, ethyl acetate, acetone, methyl ethyl ketone, etc.

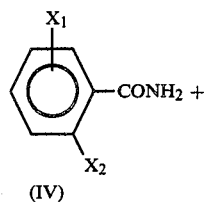
(IV)

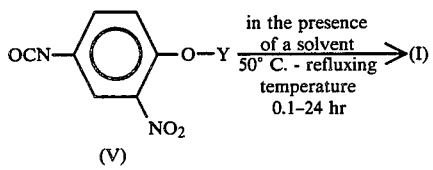
(V)

In the formula, $X_1$, $X_2$ and Y are as defined above. As the solvent to be used for the above reaction, there may be mentioned the same solvents as mentioned above for the reaction [A].

The aniline compound of the formula III used as the starting material in the above reaction [A] may be prepared, for instance, as follows:

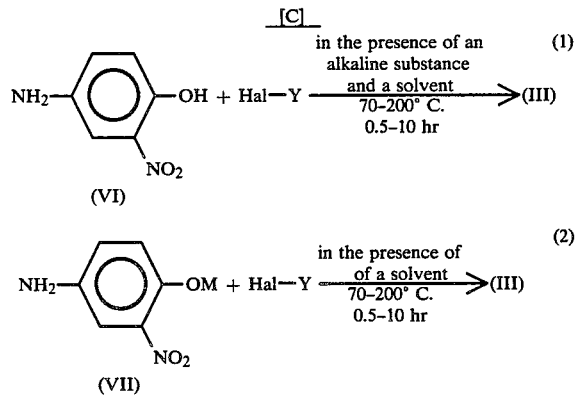

wherein Hal is a halogen atom, M is potassium or sodium, and Y is as defined above.

As the alkaline substance to be used, there may be mentioned sodium hydroxide, potassium hydroxide, sodium carbonate, potassium carbonate, sodium hydride, n-butyl lithium, etc. As the solvent, there may be mentioned an aprotic polar solvent such as dimethyl sulfoxide, dimethylformamide or hexamethylphosphoramide, a ketone such as methyl ethyl ketone or methyl isobutyl ketone, etc. This condensation reaction is preferably conducted in the atmosphere of nitrogen gas.

Further, the isocyanate compound of the formula V used as the starting material in the above reaction [B], may be prepared, for instance, as follows:

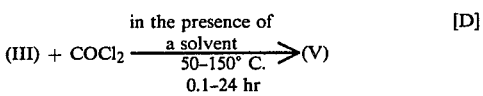

As the solvent to be used, there may be mentioned a solvent inert to phosgene, such as benzene, toluene, xylene, monochlorobenzene, dioxane, tetrahydrofuran, dimethylacetamide, ethyl acetate, acetone, methyl ethyl ketone, etc.

Now, specific examples for the synthesis of the compounds of the present invention will be described.

SYNTHETIC EXAMPLE 1

Synthesis of N-(2-nitrobenzoyl)-N'-[4-(5-trifluoromethyl-2-pyridyloxy)-3-nitrophenyl]urea (Compound No. 9)

(1) Synthesis of 4-(5-trifluoromethyl-2-pyridyloxy)-3-nitroaniline 1.28 g of 4-amino-2-nitrophenol and 0.33 g of sodium hydroxide were dissolved in 10 ml of water, and then water was completely distilled off. 1.36 g of 2-chloro-5-trifluoromethylpyridine and 20 ml of dimethyl sulfoxide were added thereto, and the mixture was reacted in the atmosphere of nitrogen gas at 170° C. for 4.5 hours. After the completion of the reaction, the reaction product was poured into water, and extracted with ethyl acetate. The extract was washed with water and dried over anhydrous sodium sulfate, and purified by silica gel column chromatography, whereupon 1.05 g of 4-(5-trifluoromethyl-2-pyridyloxy)-3-nitroaniline having a melting point of from 95° to 105° C. was obtained.

(2) Synthesis of N-(2-nitrobenzoyl)-N'-[4-(5-trifluoromethyl-2-pyridyloxy)-3-nitrophenyl]urea 1.00 g of 4-(5-trifluoromethyl-2-pyridyloxy)-3-nitroaniline obtained in the above step (1) was dissolved in 10 ml of dioxane. The solution was dropwise added to 10 ml of a dioxane solution containing 0.96 g of 2-nitrobenzoyl isocyanate, and the mixture was reacted at room temperature for 16 hours. After the completion of the reaction, the reaction product was poured into water, and separated by filtration. The obtained crystals were washed with ethyl acetate. After distilling-off the solvent under reduced pressure, the ethyl acetate washing solution was purified by silica gel column chromatography. The purified product from the washing solution was joined to the crystals obtained as above, whereby 0.85 g of the desired product having a melting point of from 194° to 198° C. was obtained.

SYNTHETIC EXAMPLE 2

Synthesis of
N-(2-nitrobenzoyl)-N'-[4-(5-bromo-2-pyrimidinyloxy)-3-nitrophenyl]urea (Compound No. 3)

(1) Synthesis of 4-(5-bromo-2-pyrimidinyl)-3-nitroaniline 1.94 g of 5-bromo-2-chloropyrimidine and 1.93 g of sodium 4-amino-2-nitrophenolate were dissolved in 20 ml of dimethylformamide, and reacted in the atmosphere of nitrogen gas at 150° C. for 5 hours. After the completion of the reaction, the reaction product was poured into water, and extracted with ethyl acetate. The extract layer was washed with brine and dried over anhydrous sodium sulfate, and purified by silica gel column chromatography, whereby 1.35 g of 4-(5-bromo-2-pyrimidinyl)-3-nitroaniline having a melting point of 165° to 167° C. was obtained.

(2) Synthesis of N-(2-nitrobenzoyl)-N'-[4-(5-bromo-2-pyrimidinyloxy)-3-nitrophenyl]urea 1.32 g of 4-(5-bromo-2-pyrimidinyl)-3-nitroaniline obtained in the above step (1), was dissolved in 10 ml of dioxane. The solution was dropwise added to 10 ml of a dioxane solution containing 1.23 g of 2-nitrobenzoyl isocyanate, and the mixture was reacted at room temperature for 17 hours.

After the completion of the reaction, the reaction product was poured into water and collected by filtration, and then washed sequentially with hot water, with methanol and with ethyl acetate, whereby 1.09 g of the desired product having a melting point of from 222° to 224° C. was obtained.

SYNTHETIC EXAMPLE 3

Synthesis of
N-(2-nitrobenzoyl)-N'-[4-(5-chloro-2-pyrimidinyloxy)-3-nitrophenyl]urea (Compound No. 2)

(1) Synthesis of 4-(5-chloro-2-pyrimidinyl)-3-nitroaniline 1.43 g of 2,5-dichloropyrimidine was dissolved in 20 mol of dimethyl sulfoxide. To this solution, a mixture of 1.50 g of 4-amino-2-nitrophenol and 5 ml of water, and 2.69 g of potassium carbonate were added, and the mixture was reacted in the atmosphere of nitrogen gas at a temperature of from 100° to 110° C. for 2 hours. After the completion of the reaction, the reaction product was poured into water, and extracted with methylene chloride. The extract layer was washed with brine and dried over anhydrous sodium sulfate, and purified by silica gel column chromatography, whereby 0.74 g of 4-(5-chloro-2-pyrimidinyl)-3-nitroaniline having a melting point of from 151° to 152° C., was obtained.

(2) Synthesis of N-(2-nitrobenzoyl)-N'-[4-(5-chloro-2-(pyrimidinyloxy)-3-nitrophenyl]urea 0.60 g of 4-(5-chloro-2-pyrimidinyl)-3-nitroaniline obtained in the above step (1), was dissolved in 8 ml of dioxane. The solution was dropwise added to 6 ml of a dioxane solution containing 0.40 g of 2-nitrobenzoyl isocyanate, and the mixture was reacted at room temperature for 15 hours.

After the completion of the reaction, the reaction product was poured into water and collected by filtaration, and then washed sequentially with hot water, with methanol and with ethyl acetate, whereby 0.90 g of the desired product having a melting point of from 211° to 213° C. was obtained.

SYNTHETIC EXAMPLE 4

Synthesis of
N-(2-nitrobenzoyl)-N'-[4-(6-bromo-3-pyridazinyloxy)-3-nitrophenyl]urea (Compound No. 7)

3.0 g of 3,6-dibromopyridazine was dissolved in 15 ml of dimethyl sulfoxide. To this solution, a mixture of 2.0 g of 4-amino-2-nitrophenol, 3.6 g of potassium carbonate and 10 ml of water was added and, after flushing with nitrogen, the mixture was reacted at a temperature of from 100° to 110° C. for 2 hours. After the completion of the reaction, the reaction product was cooled and poured into water, and then extracted with methylene chloride. The extract layer was washed with an aqueous sodium hydroxide solution and then with water, and dried over anhydrous sodium sulfate. Then, the solvent was distilled off, whereby 2.4 g of 4-(6-bromo-3-pyridazinyloxy)-3-nitroaniline was obtained. (2) 1.0 g of 4-(6-bromo-3-pyridazinyloxy)-3-nitroaniline obtained in the above step (1) was dissolved in 20 ml of dioxane. To this solution, 8 ml of a dioxane solution containing 0.62 g of 2-nitrobenzoyl isocyanate was added, and the mixture was reacted at room temperature for 15 hours. After the completion of the reaction, the reaction product was poured into water and collected by filtration. The obtained solid was dried and, after the addition of methylene chloride, again subjected to filtration, whereby 1.0 g of the desired product having a melting point of from 222° to 225° C. was obtained.

The representative compounds of the present invention are listed below.

Compound No. 1:
N-(2-nitrobenzoyl)-N'-[4-(5-iodo-2-pyrimidinyloxy)-3-nitrophenyl]urea
m.p. 232°–235° C.

Compound No. 2:
N-(2-nitrobenzoyl)-N'-[4-(5-chloro-2-pyrimidinyloxy)-3-nitrophenyl]urea
m.p. 211°–213° C.

Compound No. 3:
N-(2-nitrobenzoyl)-N'-[4-(5-bromo-2-pyrimidinyloxy)-3-nitrophenyl]urea
m.p. 222°–224° C.

Compound No. 4:
N-(2-chlorobenzoyl)-N'-[4-(5-chloro-2-pyrimidinyloxy)-3-nitrophenyl]urea
m.p. 193°–196.5° C.

Compound No. 5:
N-(2,4-dinitrobenzoyl)-N'-[4-(5-chloro-2-pyrimidinyloxy)-3-nitrophenyl]urea
m.p. 255°–257.5° C. (dec.)

Compound No. 6:
N-(4-chloro-2-nitrobenzoyl)-N'-[4-(5-chloro-2-pyrimidinyloxy)-3-nitrophenyl]urea
m.p. 222°–225° C.

Compound No. 7:
N-(2-nitrobenzoyl)-N'-[4-(6-bromo-3-pyridazinyloxy)-3-nitrophenyl]urea
m.p. 222°–225° C.

Compound No. 8:
N-(2,4-dinitrobenzoyl)-N'-[4-(6-chloro-3-pyridazinyloxy)-3-nitrophenyl]urea Compound Nb. 9:

N-(2-nitrobenzoyl)-N'-[4-(5-trifluoromethyl-2-pyridyloxy)-3-nitrophenyl]urea
m.p. 194°–198° C.

Compound No. 10:
N-(2-nitrobenzoyl)-N'-[4-(5-chloro-2-pyridyloxy)-3-nitrophenyl]urea
m.p. 190°–193° C.

Compound No. 11:
N-(2-trifluoromethylbenzoyl)-N'-[4-(5-chloro-2-pyrimidinyloxy)-3-nitrophenyl]urea Among the aniline compounds and the isocyanate compounds represented by the above formulas III and V, those represented by the following formula VII are believed to be novel compounds.

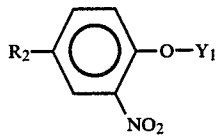

(VII)

wherein $R_2$ is an amino group or an isocyanate group, and $Y_1$ is

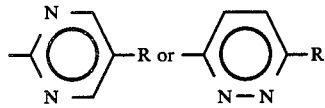

(wherein R is a hydrogen atom, a halogen atom or a trifluoromethyl group).

In the formula VII, $R_2$ is preferably an amino group, and R is preferably a halogen atom or a trifluoromethyl group. Particularly preferred is the one wherein R is a halogen atom.

The intermediate compound of the formula VII can be converted to the N-benzoyl-N'-(3-nitrophenyl) urea compound of the formula I, which is useful with high antitumour activities.

Now, the antitumour activities, acute toxicity, doses and administration routes of the N-benzoyl-N'-(3-nitrophenyl) urea compounds of the present invention will be described.

(1) Antitumour activities

Test Example 1 (Intraperitoneal-intraperitoneal)

To $BDF_1$ mice, p-388 leukemia cells were intraperitoneally inoculated in an amount of $1 \times 10^6$ cells/mouse. A test drug was intraperitoneally administered twice, i.e. one day and four days after the inoculation. The mice were observed for 30 days for survival or death. The increase life span ILS (%) of each treated group was obtained with the number of survival days of mice of the control group to which a physiological saline was administered, being evaluated as 0. The results are shown in Tables 1-1 to 1-3. The drugs were dispersions obtained by adding small amounts of surfactants (e.g. Tween-80) to the test compounds.

TABLE

| Compound No. | Dose (Active ingredient mg/kg/day) | ILS* (%) |
|---|---|---|
| 1-1 (Pyrimidine compounds) | | |
| 1 | 50 | 111 |
| 2 | 50 | 134 |
| 3 | 50 | 120 |
| 4 | 100 | 102 |

TABLE -continued

| Compound No. | Dose (Active ingredient mg/kg/day) | ILS* (%) |
|---|---|---|
| 6 | 25 | 165 |
| Comparative Compound No. 1 | 100 | 33 |
| Comparative Compound No. 2 | 100 | 65 |
| 5-Fluorouracil | 60 | 85 |
| 1-2 (Pyridazine compounds) | | |
| 7 | 100 | 152 |
| Comparative Compound No. 3 | 200 | 24 |
| Comparative Compound No. 4 | 100 | 36 |
| 1-3 (Pyridine compounds) | | |
| 9 | 100 | 119 |
| 10 | 100 | 153 |
| Comparative Compound No. 5 | 100 | 70 |
| Comparative Compound No. 6 | 200 | 50 |

Notes:
ILS (%)*: Increase Life Span, calculated in accordance with the following formula: ILS (%) = MST-100, where MST is the ratio of median survival time of test and control animals.
Comparative Compound No. 1: N—(2-chlorobenzoyl)-N'—[3-chloro-4-(5-chloro-2-pyrimidinyloxy)phenyl]urea, disclosed in Japanese Unexamined Patent Publication No. 109721/1982.
Comparative Compound No. 2: N—(2-bromobenzoyl)-N'—[3-chloro-4-(5-iodo-2-pyrimidinyloxy)phenyl]urea, disclosed in the same publication.
Comparative Compound No. 3: N—(2-chlorobenzoyl)-N'—[3-chloro-4-(6-chloro-3-pyridazinyloxy)phenyl]urea, disclosed in Japanese Unexamined Patent Publication No. 15272/1981.
Comparative Compound No. 4: N—(2-chlorobenzoyl)-N'—[4-(6-bromo-3-pyridazinyloxy)-3-chlorophenyl]urea, included in the same publication.
Comparative Compound No. 5: N—(2-nitrobenzoyl)-N'—[3-chloro-4-(5-trifluoromethyl-2-pyridyloxy)phenyl]urea, disclosed in Japanese Unexamined Patent Publication No. 109721/1982.
Comparative Compound No. 6: N—(2-chlorobenzoyl)-N'—[4-(5-bromo-2-pyridyloxy)-3-chlorophenyl]urea, disclosed in the same publication.

Test Example 2 (intraperitoneal-oral)

To $BDF_1$ mice, p-388 leukemia cells were intraperitoneally inoculated in an amount of $1 \times 10^6$ cells/mouse. A test drug was orally administered twice i.e. one day and four days after the inoculation. The mice were observed for 30 days for survival or death, and the ILS (%) of each treated group was obtained with the number of survival days of mice of the control group to which a physiological saline was administered, being evaluated as 0. The results are shown in Table 2. The test drugs and comparatives drugs were formulated in accordance with Formulation Example 4 given hereinafter.

TABLE 2

| Compound No. | Dose (Active ingredient mg/kg/day) | ILS (%)* |
|---|---|---|
| (Pyrimidine compounds) | | |
| 2 | 400 | 108 |
| | 200 | 90 |
| 3 | 400 | 46 |
| | 200 | 39 |
| Comparative Compound No. 1 | 1600 | 24 |
| | 800 | 11 |
| Comparative Compound No. 2 | 800 | 2 |
| | 400 | 4 |
| Comparative Compound No. 7 | 1600 | 41 |

Notes:
ILS (%)° and Comparative Compound Nos. 1 and 2 are the same as mentioned above in the notes of Table 1.
Comparative Compound No. 3: N—(2-nitrobenzoyl)-N'—[3-chloro-4-(5-iodo-2-pyrimidinyloxy)phenyl]urea, disclosed in Japanese Unexamined Patent Publication No. 109721/1982.

As is evident from the comparative data in Test Example 2, the compounds of the present invention have remarkably high antitumour activities as compared with the comparative compounds. The reason is not clearly understood, but it is assumed that due to the differences in the absorption of the drugs by the gut, the drug concentrations in blood and the transfer property of the drugs to the target portions, there may be substantial difference in the arrival of the drugs to the diseased portions, whereby a substantial difference in the antitumour activities is brought about.

(2) Acute Toxicity

To ddY mice (10 animals), a drug containing one of Compound Nos. 1-4, 7, 9 and 10 of the present invention formulated in accordance with Formulation Example 4 was intraperitoneally administered, and the $LD_{50}$ value was measured and found to be at least 100 mg/kg in each case, and the $LD_{50}$ value of Compound No. 6 of the invention found to be at least 50 mg/kg.

(3) Doses and Administration Routes

As to administration routes in the case of animals, the compounds of this invention are administered as injections such as intraperitoneal injection, intravenous injection, local injection and the like, or as oral drugs. In the case of human beings, said compounds are administered as injections such as intravascular (intravenous or intraarterial) injection, local injection and the like, or oral drugs, suppositories or the like. As to the dose, said compounds are administered continuously or intermittently in a range in which the total dose does not exceed a certain level, in consideration of the results of animal experiments and various conditions. However, the dose may, of course, be properly varied depending on the administration route and on the conditions of a patient or an animal to be treated (for example, age, body weight, sex, sensitivity, food and the like), interval of administration, drugs used in combination with said compounds and the degree of disease. An optimum dose and the number of administrations under certain conditions should be determined by medical specialists.

The antitumorous composition of this invention are prepared in the same manner as for conventional drugs. For example, they are prepared from an active ingredient and various pharmacologically acceptable adjuvants such as inactive diluent and the like. Oral and intravenous administration of these antitumorous compositions is most suitable. The content of the active ingredient in the antitumorous compositions of this invention may vary depending on various conditions and cannot be determined uniquely. It is sufficient that the active ingredient is contained similarly to the case of conventional antitumorous compositions.

The compounds of the present invention are hardly soluble in both water and organic solvents. Therefore, they are preferably formulated into an aqueous suspension which may further contain phospholipids. As a method for producing an aqueous suspension containing no phospholipids, there may be mentioned a method wherein, if necessary, the active compound is preliminarily pulverized into fine powder, then the fine powder of the active compound is added to an aqueous solution containing a surfactant and, if necessary, a defoaming agent, the mixture is pulverized in a wet system until all particles have a particle size of not higher than 5 μm, more preferably not higher than 2 μm (80% of particles), and a thickener is added thereto. As specific examples of the surfactant, there may be mentioned an oxyethylated polyarylphenol phosphate, a polyoxyethylene hardened castor oil, a polyoxyethylene sorbitan fatty acid ester, a sugar ester, a polyoxyethylene polyoxypropylene block polymer, etc. As specific examples of the defoaming agent, there may be mentioned dimethylpolysiloxane, methylphenylsiloxane, a sorbitan fatty acid ester, a polyoxyethylene-polyoxypropylene cetyl ether, silicone, etc. As specific examples of the thickener, there may be mentioned guar gum, alginic acid, gum arabic, pectin, starch, xanthane gum, gelatin, etc. On the other hand, as a method for preparing an aqueous suspension containing a phospholipid, there may be mentioned a method wherein a phospholipid such as soybean phospholipid or yolk phospholipid is used instead of the surfactant in the above-mentioned method, and an antioxidant such as α-tocopherol is used instead of the thickener.

Further, these compounds may be formulated into tablets, capsules, enteric agents, granules, powders, injection solutions or suppositories by common methods for formulations.

Now, Formulation Examples of the antitumour drugs of the present invention will be described.

Formulation Example 1

70 mg of a non-crystalline powder of the above Compound No. 9 was thoroughly mixed with 30 mg of lactose, and 100 mg of the mixture was filled into a capsule to obtain a capsule drug for oral administration.

Formulation Example 2

85 parts by weight of a non-crystalline powder of the above Compound No. 7 was uniformly mixed with 1 part by weight of glucose, 10 parts by weight of corn starch and 1.5 parts by weight of a 5% starch paste, and the mixture was granulated by a wet method. Then, 1 part by weight of magnesium stearate was added thereto. The mixture was tableted to obtain tablets for oral administration.

Formulation Example 3

5 g of the above Compound No. 5 was dissolved in 5 ml of dimethylacetamide, and 25 ml of coconut oil, 7 g of Pegnol HC-17 (manufactured by Toho Kagaku K.K.) and 6 g of HO-10M (manufactured by Toho Kagaku K.K.) were added to obtain an emulsion. To this emulsion, the same amount of sterilized distilled water was added, and the mixture was subjected to ultrasonic treatment for from 20 to 30 seconds to obtain an oily suspension.

Formulation Example 4

The Compound No. 2 of the present invention was preliminarily pulverized by a centrifugal pulverizer. On the other hand, 5 parts by weight of polyoxyethylene (60) hardened castor oil, 0.2 part by weight of silicone and 0.3 part by weight of a polyoxyethylene-polyoxypropylene block polymer were added to 79.5 parts by weight of a physiological saline to obtain an aqueous solution, to which 10 parts by weight of the above pulverized Compound No. 2 of the present invention was added. The mixture was pulverized in a wet system by a sand mill using glass beads (80% of particles having a particle size of not larger than .2 μm). Then, 5 parts by weight of xanthane gum (2% solution) was added thereto to obtain an aqueous suspension.

Formulation Example 5

To an aqueous solution obtained by dissolving 1.5 parts by weight of oxyethylated polyarylphenol phosphate and 0.2 part by weight of silicone in 53.3 parts by weight of a physiological saline, 40 parts by weight of the Compound No. 3 of the present invention was added, and the mixture was pulverized in a wet system in the sand mill by using glass beads (90% of particles having a particle size of not larger than 2 μm). Then, 5 parts by weight of xanthane gum (2% solution) was added thereto to obtain an aqueous suspension.

Formulation Example 6

The Compound No. 1 of the present invention was preliminarily pulverized by a centrifugal pulverizer. 5 parts by weight of the pulverized Compound No. 1 of the present invention was added to an aqueous solution obtained by stirring and dispersing 2 parts by weight of yolk phospholipid, 0.001 part by weight of α-tocopherol and 92.999 parts by weight of a physiological saline. Then, the mixture was pulverized in a wet system in a sand mill by using glass beads (80% of particles having particle size of not larger than 2 μm) to obtain an aqueous suspension.

We claim:

1. An N-benzoyl-N'-(3-nitrophenyl) urea compound having the formula:

wherein each of $X_1$ and $X_2$ is independently a hydrogen atom, a halogen atom, or a nitro group, and Y is

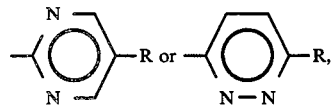

wherein R is a halogen atom.

2. The compound according to claim 1, wherein $X_1$ is a hydrogen atom.

3. The compound according to claim 1, wherein $X_2$ is a halogen atom or a nitro group.

4. The compound according to claim 1, wherein $X_2$ is a nitro group.

5. The compound according to claim 1, wherein Y is

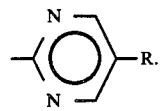

6. The compound according to claim 1, wherein $X_1$ is a hydrogen atom, $X_2$ is a nitro group, Y is

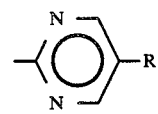

wherein R is a halogen atom.

7. The compound according to claim 1, which is N-(2-nitrobenzoyl)-N'-urea.

8. The compound according to claim 1, which is N-(2-nitrobenzoyl)-N'-urea.

9. The compound according to claim 1, which is N-(2-nitrobenzoyl)-N'-urea.

10. A composition for treating leukemia in a mammal comprising an N-benzoyl-N'-(3-nitrophenyl) urea compound as defined in claim 1 in an amount sufficient to exhibit antileukemia activity and a pharmacologically acceptable adjuvant.

11. a method for treating leukemia in a mammal which comprises administering to a mammal an N-benzoyl-N'-(3-nitrophenyl) urea compound as defined in claim 1 in an amount sufficient to exhibit antileukemia activity.

12. An intermediate compound having the formula:

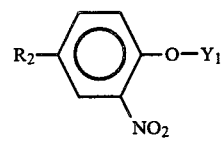

wherein $R_2$ is an amino group or an isocyanate group, and $Y_1$ is

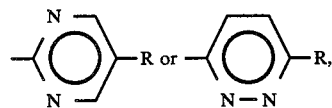

wherein R is a halogen atom.

13. The compound according to claim 12, wherein $R_2$ is an amino group, and R is a halogen atom.

* * * * *